US008142071B1

(12) United States Patent
Feller

(10) Patent No.: US 8,142,071 B1
(45) Date of Patent: Mar. 27, 2012

(54) THERMOELECTRIC THERMAL TRANSFER SENSOR

(76) Inventor: Murray F Feller, Micanopy, FL (US)

( * ) Notice: Subject to any disclaimer, the term of this patent is extended or adjusted under 35 U.S.C. 154(b) by 414 days.

(21) Appl. No.: 12/560,521

(22) Filed: Sep. 16, 2009

(51) Int. Cl.
*G01K 17/00* (2006.01)
*G01K 3/00* (2006.01)
*G01K 7/00* (2006.01)
*G01N 25/00* (2006.01)

(52) U.S. Cl. .......... 374/29; 374/110; 374/112; 374/166; 374/15

(58) Field of Classification Search .................... 374/29, 374/110, 112, 166, 15
See application file for complete search history.

(56) References Cited

U.S. PATENT DOCUMENTS

| | | | |
|---|---|---|---|
| 3,720,103 A * | 3/1973 | Adams et al. ................... 374/29 | |
| 4,774,833 A | 10/1988 | Webler et al. | |
| 4,993,842 A | 2/1991 | Morimoto et al. | |
| 5,940,784 A * | 8/1999 | El-Husayni ................... 702/130 | |
| 5,948,978 A | 9/1999 | Feller | |
| 6,023,969 A | 2/2000 | Feller | |
| 6,241,383 B1 | 6/2001 | Feller | |
| 6,443,003 B1 | 9/2002 | Bailis | |
| 2005/0078451 A1 * | 4/2005 | Sauciuc et al. ................ 361/700 |

* cited by examiner

*Primary Examiner* — Lisa Caputo
*Assistant Examiner* — Mirellys Jagan
(74) *Attorney, Agent, or Firm* — David Kiewit

(57) ABSTRACT

Thermal transfer measurements are useful for measuring either a mass flow rate or the specific heat of a fluid. Thermoelectric devices are desirable for this because of their ability to simultaneously heat one portion of the sensor while cooling another. However, the internal thermal resistance of thermoelectric devices has limited the accuracy of thermoelectric thermal transfer sensors. This problem is solved by using separate temperature sensors to measure selected temperature differences established by the thermoelectric portion of a thermal transfer sensor.

10 Claims, 3 Drawing Sheets

THERMOELECTRIC THERMAL TRANSFER SENSOR

BACKGROUND OF THE INVENTION

1. Field of the Invention

This invention relates to apparatus for and method of measuring thermal transfer between an electrically powered sensor and a fluid.

2. Background Information

Measuring thermal transfer between a thermally active sensor and a fluid allows one to derive the fluid flow rate if the fluid's specific heat is known, or to derive the fluid's specific heat if its flow rate is known. A discussion of the use of thermal transfer measurements for correcting BTU meters is provided in the inventor's co-pending U.S. patent application Ser. No. 12/499,420, filed on Jul. 8, 2009, and now issued as U.S. Pat. No. 7,775,706. The disclosure of U.S. Pat. No. 7,775,706, is incorporated herein by reference.

Bialis, in U.S. Pat. No. 6,443,003, describes a sensor for measuring changes in mass air flow. His sensor uses one or more thermoelectric modules, each of which serves both as a heat transfer element and as a differential temperature sensor. That is, the thermoelectric module generates a temperature differential when powered and generates a Seebeck voltage when a temperature differential is present and the module is not powered.

In situations where the thermal transfer rates are low, the internal thermal resistance of the thermoelectric module can be ignored and the measured Seebeck voltage is representative of the temperature differential across its plates. The internal thermal resistance of the thermoelectric module is therefore of little concern when measuring low thermal transfer rates, but becomes significant when measuring high flow rates of fluids having a substantial specific heat.

BRIEF SUMMARY OF THE INVENTION

Using separate temperature sensors to measure the temperature difference between two working plates bounding a thermoelectric device avoids having to deal with the internal thermal resistance of one or more thermoelectric modules making up the device. Thus, the invention provides a solution to the problem of thermal transfer measurement inaccuracy associated with the internal thermal resistance of a thermoelectric module (TEM). In a heat transfer sensor the magnitude of this inaccuracy increases with the flow rate and the specific heat of a fluid.

One aspect of the invention is that it provides a thermal transfer sensor comprising at least one thermoelectric module and a plurality of temperature sensors distinct from the thermoelectric module or modules. Each thermoelectric device has two parallel working plates and the external working surfaces of these plates are arranged to thermally contact a working fluid when the thermal transfer sensor is in use, and at least one of the separate temperature sensors is in thermal contact with each of the working plates and through the working plate to the working fluid. Each thermoelectric device is operable to generate a temperature differential between its working plates responsive to an electrical power input.

Another aspect of the invention is that it provides a thermal transfer fluid flow sensor operable to measure both a direction and a rate of flow of a fluid. A preferred thermal transfer sensor of this sort comprises a thermoelectric device and two pairs of temperature sensors. The thermoelectric device is oriented so that the fluid flows along the external surfaces of its working plates. A first pair of the temperature sensors is positioned adjacent one of the sides of the thermoelectric device and each of the two sensors in that pair is in thermal contact with a respective one of the working plates. The second pair of temperature sensors is spaced apart from the first pair of temperature sensors along a fluid flow line adjacent the opposite side of the thermoelectric device and each temperature sensor of the second pair are in thermal contact with a respective one of the working plates.

A further aspect of the invention is that it provides a method of using separate temperature sensors to measure thermal transfer between a fluid and a thermoelectric device comprising one or more thermoelectric modules disposed between respective working plates. To carry out this method, one provides a plurality of temperature sensors, separate from the thermoelectric device and adjacent or abutting it. Each of these temperature sensors has a respective output representative of a temperature of a respective one of the working plates. The method also comprises the steps of applying respective electrical power inputs to each thermoelectric module to heat one of its working plates while cooling the other, and then determining, from the outputs of the temperature sensors, a respective temperature differential between respective working plates, where the measured temperature differential is unaffected by the internal thermal resistance of the TEM. In a particular preferred variation of this method both plates of the TEM are thermally linked to a working fluid through separate thermal conductors and the separate temperature sensors measure at least one of a temperature differential from one end of the conductor-TEM-conductor stack to another and a composite temperature differential obtained by separately measuring the temperature differentials along each of the two conductors. This latter measurement approach can provide more linear and stable measurements, as will be disclosed further herein.

Although it is believed that the foregoing rather broad summary description may be of use to one who is skilled in the art and who wishes to learn how to practice the invention, it will be recognized that the foregoing recital is not intended to list all of the features and advantages. Those skilled in the art will appreciate that they may readily use both the underlying ideas and the specific embodiments disclosed in the following Detailed Description as a basis for designing other arrangements for carrying out the same purposes of the present invention and that such equivalent constructions are within the spirit and scope of the invention in its broadest form. Moreover, it may be noted that different embodiments of the invention may provide various combinations of the recited features and advantages of the invention, and that less than all of the recited features and advantages may be provided by some embodiments.

DETAILED DESCRIPTION OF A PREFERRED EMBODIMENT

In studying this Detailed Description, the reader may be aided by noting definitions of certain words and phrases used throughout this patent document. Wherever those definitions are provided, those of ordinary skill in the art should understand that in many, if not most instances, such definitions apply to both preceding and following uses of such defined words and phrases.

One distinction of note is between a thermoelectric device and a thermoelectric module (TEM). The term "thermoelectric module" is used conventionally to denote an array of semiconducting thermocouples disposed between two plates that electrically isolate the module while allowing it to be thermally coupled to its environment. For example, some of the embodiments described later herein, as well as embodiments described in the inventor's earlier U.S. Ser. No. 12/499, 420, now U.S. Pat. No. 7,775,706, use a Model TE-31-0.6-1.0 thermoelectric module, supplied by T E Technology of Traverse City, Mich. The term "thermoelectric device" is used herein to denote a device comprising one or more thermoelectric modules. A "thermoelectric device" may thus be a parallel arrays of TEMS (which can provide a larger active area); or a series array of TEMS (in which the individual TEMS may be arranged and controlled so that their temperature differentials add together to provide a greater temperature differential for a given power input). In the foregoing, a 'series array' stands for a set of stacked or juxtaposed TEMs arranged so that the two TEMs at the ends of the array have one module plate that serves as a working plate and one module plate that is in thermal contact with another of the TEMS in the array. Correspondingly, each TEM that is not at an end of an array will have two module plates that are in respective thermal contact with two other TEMs. The reader will note that in most of the embodiments described herein the arrangements are more simple and the thermoelectric device is a single TEM that is described as such.

When an individual TEM is used as a thermoelectric device its plates are coupled to a working fluid, or other environment, either directly, or through additional thermal conductors. However, when one considers multi-TEM thermoelectric devices one needs to recognize that some of the plates of individual TEMs are thermally coupled to other TEMs in the device rather than being coupled to the environment. Thus, we choose to make a distinction between a "module plate" associated with an individual TEM and a "working plate" that contacts a working fluid directly or through an intermediate thermal conductor that is not a TEM. As noted above, a thermoelectric device may comprise a single TEM, in which case there is no distinction between a "module plate" and a "working plate".

Figure 1:
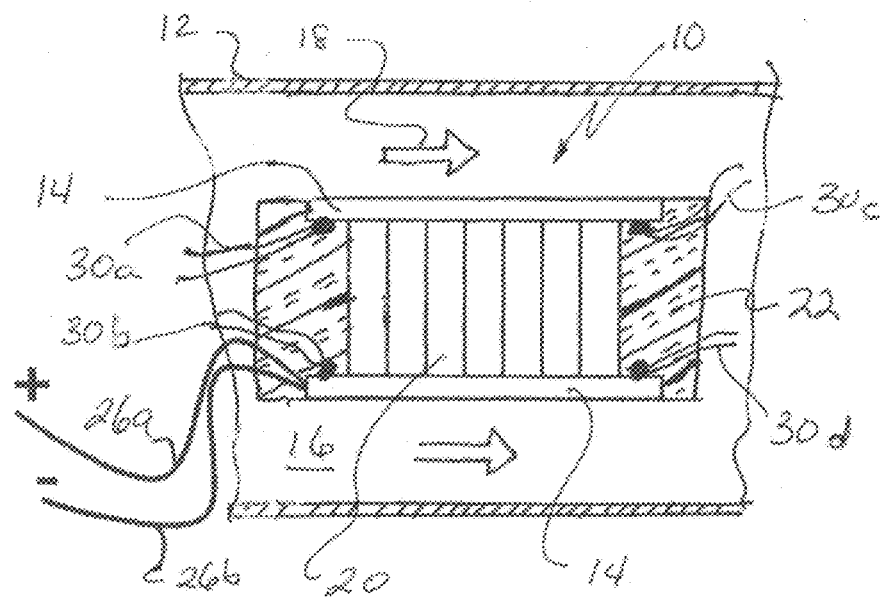
FIG. 1 is a partly schematic, partly sectional view of a first embodiment of a heat transfer sensor comprising two pairs of temperature sensors.

In FIG. 1, a thermoelectric device 10 comprising a single TEM 20 is mounted in a pipe 12 so that two working plates 14 are in direct contact with a fluid 16 flowing in a direction indicated by large open arrows 18. In this arrangement the thermoelectric module 20 has an environmentally protective and thermally isolating barrier 22 surrounding it so that only the working plates 14 are in thermal contact with the fluid 16. As is known in the art, such a sensing assembly may be supported on the end of a probe tube 24, as is depicted for other sensor geometries in FIGS. 3-5. The electrical leads 26a, 26b for powering the TEM 20 and the four temperature sensors, 30a, 30b, 30c, 30d, are all depicted schematically in the interest of clarity of presentation.

When used for sensing flow of a fluid 16 having a high thermal conductivity, such as water, the arrangement depicted in FIG. 1 may lead to high input power requirements at high flow rates. The thermal resistance of the TEM 20 at high heat transfer rates may be great enough to introduce serious non-linearities if one measures the temperature differential between the plates 14 by measuring a Seebeck voltage at the power leads 26a, 26b during periods when power is not applied. This problem can be avoided by using temperature sensors, generally denoted with a subscripted reference numeral 30, other than the TEM itself, to measure the temperatures of the plates and thereby determine the temperature differential.

Separate temperature sensors, in order to be beneficial, must be physically small and of low mass in order to minimize changes in the TEM'S response to the fluid while accurately sensing the plate temperature. A wide variety of such temperature sensors are known in the art, and many of these are compatible with the present invention. The separate temperature sensors used to measure the temperatures of the working plates may be, without limitation, resistance temperature detectors (RTDs), positive or negative coefficient of resistance thermistors, thermocouples, etc.

Figure 2:
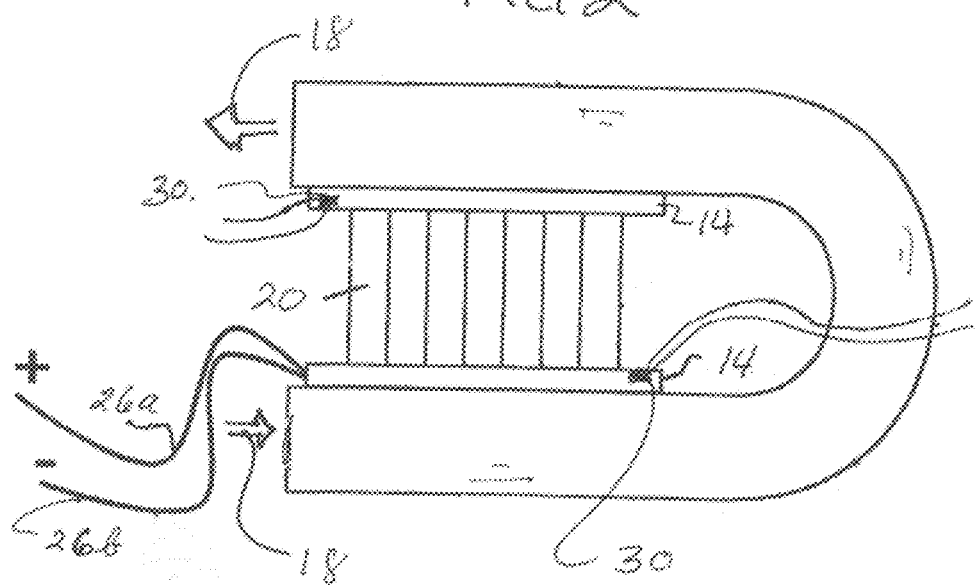
FIG. 2 is a partly schematic elevation view of a second embodiment of a heat transfer sensor comprising a single pair of temperature sensors.
Figures 3, 4:
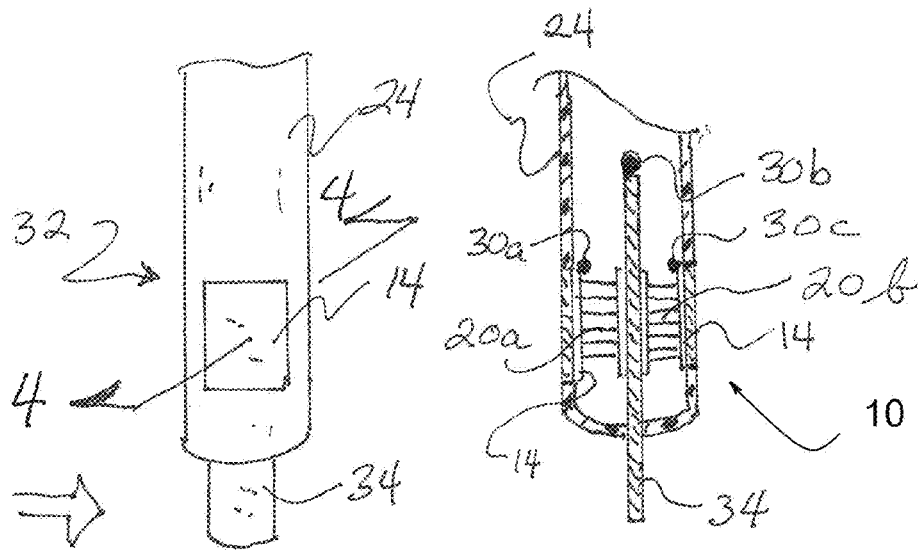
FIG. 3 is an elevation view of a probe of the invention having three temperature sensors and a thermally conductive vane aligned with a flow direction.
FIG. 4 is a partly schematic sectional view of the probe of FIG. 3, where the section is indicated by the arrow 4-4 in FIG. 3.

When using separate temperature sensors to measure a temperature differential associated with a TEM, one needs at least two temperature sensors (e.g., as depicted in FIG. 2). However, there are many situations in which more than two sensors can be used. Turning to FIG. 3, one finds a schematically depicted sensing head portion 32 of a thermal transfer probe having two TEMs 20a, 20b, each of which has one of its module plates in thermal contact with a common central working plate 34 that may be configured as a vane extending into the fluid. These TEMS are preferably operated so that their respective temperature changes sum. In this depiction, three temperature sensors 30a, 30b, 30c, are used to measure two temperature differentials generated by the two TEMs 20a, 20b. It may be noted, however, that one could also use this configuration, or one like it in which there was no separate central vane, in a mode in which only the two outer temperature sensors 30a, 30c, are used to measure the overall temperature change, which is the sum of the temperature differentials associated with each of two TEMs. Because TEMs are generally more efficient when generating lower individual temperature differences, series connected arrangements of this sort can provide a thermoelectric device that produces a higher overall temperature difference while operating efficiently.

Independent temperature sensors mounted on the working plates can lead to errors if the temperature sensors are not located so as to primarily sense the fluid temperature change over the full range of conditions experienced. These sensors are typically located near the downstream, or trailing, end of a TEM and therefore respond to both plate and fluid temperature.

Figure 5:
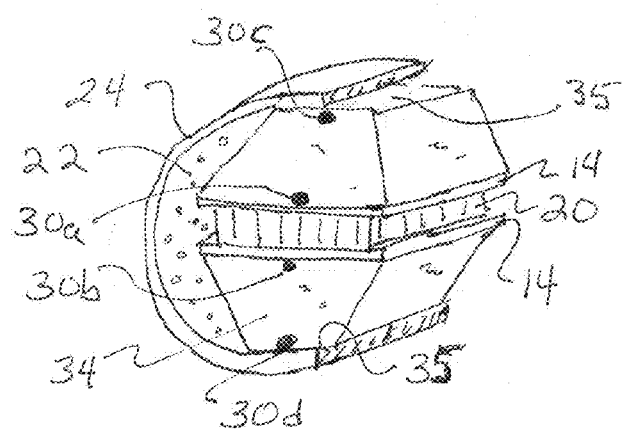
FIG. 5 is a partly schematic cut-away view of an embodiment of the invention having thermal conductors interposed between the contact faces of a thermoelectric device and a measured ambient.

As depicted in FIG. 1, the plates 14, of the TEM 20 are in direct contact with the fluid 16 but other portions of the TEM are isolated from the fluid by an insulator 22. The unobstructed thermal path to the working plate 14 provides the greatest sensitivity and widest dynamic range of the thermal transfer sensor. Turning now to FIG. 5, one finds a schematically depicted portion of a thermal transfer sensor comprising a TEM 20 and two temperature sensors 30c, 30d, each of which is separated from a respective working plate 14 by a thermal conductor 34 (e.g., an aluminum block). The shape of the thermal conductor both facilitates inserting the transfer sensor into a thin-walled probe tube 24 and minimizes the effects of spatial inhomogeneity in thermal output across the TEM. In a preferred arrangement thermal insulation 22 is provided to prohibit thermal contact between a working fluid and the sidewalls of the TEM—i.e., the only thermal path allowed for linking the TEM to the working fluid is through the conductors 34 and the portions of the tube 24 immediately abutting the distal ends of the conductors. The tube may be omitted if the insulator and conductor can survive contact with the fluid.

It will be understood that in using the thermal transfer sensor configuration of FIG. 5, one can measure a temperature differential solely by means of the two temperature sensors 30c, 30d distal from the TEM, or one can combine these with a measurement of the Seebeck voltage of the TEM. Additionally, if one supplies two temperature sensors 30a, 30b adjacent the interface between the TEM and the thermal conductor, one can measure a temperature differential across one or both of the thermal conductors. Inasmuch as the thermal properties of the conductor (e.g., an aluminum block) are more stable and more linear than are those of the TEM itself, this arrangement can provide superior accuracy.

In measuring the differential temperature across a TEM, the temperature sensors may be arranged in a bridge circuit having an output for controlling power to the TEM to maintain a selected differential fluid temperature. The power delivered to the TEM thus varies with heat transfer rates and can be used as the output signal to the processor for scaling and compensation as may be required for a specific application. The power supplied to the TEM could be maintained constant and the fluid differential temperature sensor signal used as the heat transfer output signal. The difference between the TEM and fluid differential signals is also usable as a heat transfer output signal with either the fluid differential temperature or TEM power being maintained constant.

In some applications one desires to measure the direction of flow, as well as its magnitude. A sensor of the invention can be configured, as depicted in FIG. 1, so that upstream 30a, 30b and downstream 30c, 30d pairs of temperature sensors are separated by the TEM along a selected flow direction 18. In this arrangement the temperature differential sensed on the downstream side of the TEM is expected to be larger than that measured on the upstream side. Thus, the direction of flow can be determined and fluid flow can be measured for both directions of flow. In this arrangement, whichever pair of temperature sensors establishes the greater temperature differential is used to control the power to the TEM.

Figure 6:
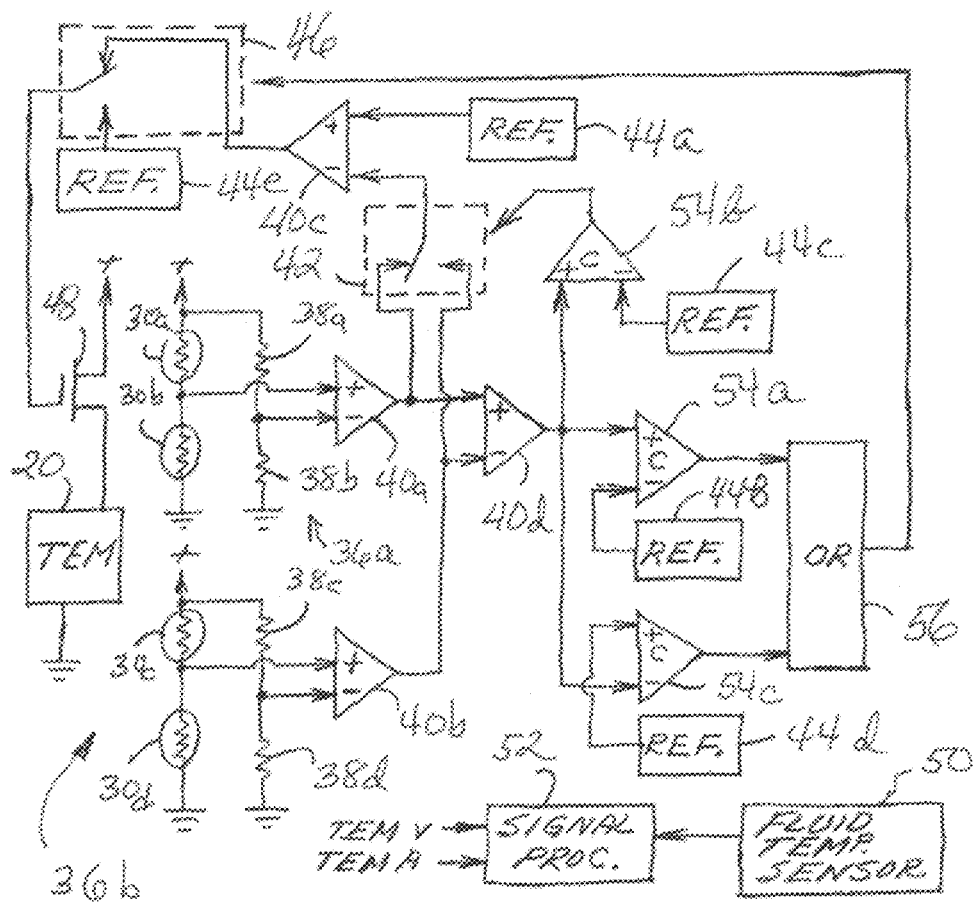
FIG. 6 is a block diagram of a thermal sensor of the invention.

Turning now to FIG. 6, one finds a block diagram of a preferred circuit. In this case, a first pair of temperature sensors 30a, 30b is arranged in a bridge circuit 36a that also comprises two resistors 38a, 38b. An output from the bridge 36a is supplied to a differential amplifier 40a having an output to the closed contact of a relay 42. Similarly, a second pair of temperature sensors 30c, 30d are arranged in a second bridge circuit 36b with another two resistors 38c, 38d connected to a second differential amplifier 40b having an output to the open contact of the relay 42. The pole output of the relay 42 is connected to the negative input of a third differential amplifier 40c where it is differentially compared with a first reference voltage 44a. The output of the third differential amplifier 40c is connected to the closed contact of a second relay 46. The pole output of the second relay 46 is connected to a FET 48 which controls the power provided to the TEM 20.

This arrangement provides a negative feedback control circuit whereby an increase in power to the TEM 20 results in an increased sensor differential temperature which reduces the signal to the FET 48, thereby maintaining the differential temperature constant. In typical operation with a flowing fluid, the power to the TEM 20 is controlled to produce a selected differential temperature, sensed by sensors 30a, 30b, which is maintained constant at a level determined by a reference voltage 44a. This negative feedback loop operates over a range of heat transfer rates corresponding to flow rates. The TEM power providing heat transfer to the fluid is the primary signal used to establish the flow rate of the fluid. That power and any correction signals, such those generated by a separate fluid temperature sensor 50 to account for fluid temperature variations, are input to a signal processor 52 to provide the output signal.

When fluid is flowing in a sensor having two pairs of temperature sensors, the sensors of the upstream pair (e.g., sensors 30c, 30d) are close to the same temperature because they primarily sense the temperature of the fluid upstream of the TEM, before the TEM has had an opportunity to make thermal transfer to the fluid and change its temperature. The output from the differential amplifier 40b connected to these sensors is relatively low compared to that from the differential amplifier 40a connected to the downstream sensor pair 30a, 30b. Thus, the output from a fourth differential amplifier 40d connected to the outputs of the first two differential amplifiers 40a, 40b is also relatively high. Comparing the output of the fourth differential amplifier to a voltage reference 44b by means of a comparator 54a produces a control signal for controlling the relay 46. When the flow is from the opposite direction, the output signal from the second differential amplifier 40b is greater than that from the first amplifier 40a so that the output from the fourth amplifier 40d is relatively low compared to that of the reference 44b, thus controlling the pole of the relay 46 to switch to the other contact. The negative feedback circuit controlling the power to the TEM thus becomes responsive to the sensors 30c, 30d, which became the downstream sensor pair when the flow direction reversed.

When there is little or no movement of the fluid, there may be uncertainty as to how the circuit will operate because the temperature sensors may not accurately sense the TEM plate temperatures. To resolve this issue, the output from the fourth amplifier 40d is also provided to two comparators 54a, 54c, which are referenced to respective voltage references 44b, 44d. The comparators 54a, 54c provide respective outputs to an OR circuit 56 to form a window detector. When neither of the sensor pairs 30a, 30b and 30c, 30d exhibit a large enough temperature differential, a LOW is outputted to a relay 46 which switches so that the FET 48 is controlled by another reference voltage 44e. The FET 48 then powers the TEM 20 at a level which can establish a temperature sensor differential temperature great enough for one of the comparators to switch state and to enable the relay 46 to switch state so that operation in a typical operating mode can be resumed.

Although the present invention has been described with respect to several preferred embodiments, many modifications and alterations can be made without departing from the invention. Accordingly, it is intended that all such modifications and alterations be considered as within the spirit and scope of the invention as defined in the attached claims.

The invention claimed is:

1. A thermal transfer sensor comprising two thermoelectric devices and three temperature sensors distinct from the thermoelectric devices, wherein:

the two thermoelectric devices are in thermal contact with a central working plate and are juxtaposed, in a facing relationship, on opposite sides of the central working plate, each thermoelectric device operable to generate a respective temperature differential between the central working plate and a respective second working plate distal therefrom responsive to a respective electrical power input; and wherein each of the central working plate and the respective second working plates is respectively in thermal contact with one of the three temperature sensors.

2. A thermal transfer sensor comprising a thermoelectric device and a plurality of temperature sensors distinct therefrom:

wherein the thermoelectric device comprises first and second working plates having respective external surfaces for thermally contacting a fluid, the thermoelectric device operable to generate a temperature differential between the first and second working plates responsive to an electrical power input; and wherein each of the working plates is respectively in thermal contact with at least one temperature sensor of the plurality thereof; the thermal transfer sensor further comprising a respective thermal conductor in thermal contact with each of the working plates, each thermal conductor contacted, adjacent an end distal from the associated plate, by a respective distal temperature sensor.

3. A thermal transfer sensor comprising a thermoelectric device and a plurality of temperature sensors distinct therefrom, wherein the thermoelectric device comprises first and second working plates having respective external surfaces for thermally contacting a fluid, the thermoelectric device operable to generate a temperature differential between the first and second working plates responsive to an electrical power input; and wherein each of the working plates is respectively in thermal contact with at least one temperature sensor of the plurality thereof; the sensor further comprising first and second thermal conductors respectively associated with the first and second working plates and arranged so as to be interposed between the respective working plate and the fluid when the fluid is present; and wherein at least one temperature sensor associated with each of the working plates is attached to the associated thermal conductor distal from the respective plate.

4. A thermal transfer fluid flow sensor operable to measure both a direction and a rate of flow of a fluid, the sensor comprising:

a thermoelectric device comprising first and second working plates having respective internal and external surfaces, the internal surfaces arranged in a facing relationship and separated from one another, over respective portions thereof, by semiconducting thermocouples, the thermoelectric device oriented so that the fluid flows along each of the external surfaces;

a first pair of temperature sensors, each in thermal contact with a respective one of the working plates at a first selected position;

a second pair of temperature sensors spaced apart from the first pair of temperature sensors along a direction of fluid flow, each temperature sensor of the second pair thereof in thermal contact with a respective one of the working plates; and circuitry operable to determine respective temperature differentials measured by the first and second pairs of temperature sensors responsive to a electrical power input supplied to the thermoelectric device, to compare the two temperature differentials, to determine that the direction of fluid flow is from the sensor pair having the smaller temperature differential to the pair having the larger differential, and to select the larger of the two temperature differentials as being representative of the rate of flow.

5. A thermal transfer sensor comprising a thermoelectric device and a plurality of temperature sensors distinct therefrom wherein:

the thermoelectric device comprises first and second working plates having respective external surfaces for thermally contacting a fluid, the thermoelectric device operable to generate a temperature differential between the first and second working plates responsive to an electrical power input; wherein each of the working plates is respectively in thermal contact with at least one temperature sensor of the plurality thereof; and thermally insulating material is disposed around the thermoelectric device so as to expose only the external surfaces of the working plates to the fluid while prohibiting heat transfer from other portions of the thermoelectric device.

6. The thermal transfer sensor of claim 5 comprising at least one pair of each of the temperature sensors, wherein the two temperature sensors in each pair thereof face each other across a space between the two working plates.

7. The thermal transfer sensor of claim 5 comprising exactly one pair of temperature sensors, the thermal transfer sensor oriented so that when the fluid flows along the working plates from an upstream end to a downstream end thereof, the pair of temperature sensors is adjacent the downstream end.

8. The thermal transfer sensor of claim 5 comprising two pairs of temperature sensors, the thermal transfer sensor oriented so that when the fluid flows along the working plates from an upstream end to a downstream end, a first pair of temperature sensors is adjacent the downstream end and the second pair is adjacent the upstream end.

9. The thermal transfer sensor of claim 5:

wherein the thermoelectric device comprises two thermoelectric modules, each having one module plate in thermal contact with the other thermoelectric module and each having a respective second module plate arranged as a respective working plate; and wherein the thermal transfer sensor further comprises two temperature sensors respectively thermally contacting the two working plates.

10. The thermal transfer sensor of claim 5 further comprising a control circuit operable to selectively measure the temperature differential from one of a Seebeck voltage generated by the thermoelectric device and a difference between respective outputs from at least two of the temperature sensors.

* * * * *